(12) United States Patent
David et al.

(10) Patent No.: US 8,378,694 B2
(45) Date of Patent: Feb. 19, 2013

(54) ORGANIC CHEMICAL SENSOR COMPRISING PLASMA-DEPOSITED MICROPOROUS LAYER, AND METHOD OF MAKING AND USING

(75) Inventors: Moses M. David, Woodbury, MN (US); Stefan H. Gryska, Woodbury, MN (US); Nelson B. O'Bryan, Tamworth, NH (US); Neal A. Rakow, Woodbury, MN (US); Michael S. Wendland, North Saint Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 182 days.

(21) Appl. No.: 12/681,758

(22) PCT Filed: Sep. 30, 2008

(86) PCT No.: PCT/US2008/078281
§ 371 (c)(1),
(2), (4) Date: Oct. 29, 2010

(87) PCT Pub. No.: WO2009/046011
PCT Pub. Date: Apr. 9, 2009

(65) Prior Publication Data
US 2011/0031983 A1 Feb. 10, 2011

(51) Int. Cl.
*G01R 27/26* (2006.01)
(52) U.S. Cl. .................... 324/663; 442/349; 264/423
(58) Field of Classification Search .................... None
See application file for complete search history.

(56) References Cited

U.S. PATENT DOCUMENTS

| | | | |
|---|---|---|---|
| 5,482,678 A | 1/1996 | Sittler | |
| 5,512,882 A | 4/1996 | Stetter et al. | |
| 5,767,687 A | 6/1998 | Geist | |
| 5,857,250 A | 1/1999 | Riley et al. | |
| 6,312,793 B1 | 11/2001 | Grill et al. | |
| 7,049,247 B2 | 5/2006 | Gates et al. | |
| 2006/0237310 A1 | 10/2006 | Patel et al. | |
| 2006/0246273 A1* | 11/2006 | McKeown et al. | 428/314.8 |
| 2007/0141580 A1 | 6/2007 | David et al. | |
| 2008/0160858 A1 | 7/2008 | Paolucci et al. | |

FOREIGN PATENT DOCUMENTS

JP 06-281610 * 10/1993

OTHER PUBLICATIONS

Nagai, K., et al. Poly[-(trimethylsilyl)-1-propyne] and related polymers: synthesis, proprties and functions, 2001, Progress in Polymer Science, vol. 26, pp. 721-798.*

Gerwen, P. V., et al. Nanoscaled interdigitated electrode arrays for biochemical sensors, 1998, Sensors and Actuators B, vol. 49, pp. 73-80.*

Grate, J. W., Acoustic Wave Microsensor Arrays for Vapor Sensing; Chem. Rev. 2000 (100), 2627-2648 (2000).

Silva, S.R.P.; "Microstructure of a-C", Chapter I, Introduction; in "Properties of Amorphous Carbon", p. 3; 2003, INSPEC, United Kingdom.

* cited by examiner

*Primary Examiner* — Robert Xu
(74) *Attorney, Agent, or Firm* — Kenneth B. Wood

(57) ABSTRACT

Applicant discloses a sensing element for sensing an organic chemical analyte, comprising a first electrode and a second electrode, and a microporous, hydrophobic, analyte-responsive dielectric material disposed at least in proximity to the first and second electrodes. The analyte-responsive dielectric material may be an amorphous random covalent network comprising a mean pore size of less than about 10 nm and a porosity of at least about 20%. An electrical property of the sensing element, such as capacitance, can be monitored in order to sense an organic chemical analyte.

17 Claims, 3 Drawing Sheets

ORGANIC CHEMICAL SENSOR COMPRISING PLASMA-DEPOSITED MICROPOROUS LAYER, AND METHOD OF MAKING AND USING

BACKGROUND

The ability to detect chemical analytes, especially organic chemical analytes, is important in many applications, including environmental monitoring, and the like. Such detection and/or monitoring of organic molecules may find particular use in, for example, so called End of Service Life Indicators which are desired for personal protective equipment such as respirators.

Many methods for the detection of chemical analytes have been developed, for example optical, gravimetric, microelectromechanical, and so on. In particular, sensors that monitor electrical properties such as capacitance, impedance, resistance, etc., have been developed. Often, such sensors rely on the change that occurs in the electrical properties of a material upon adsorption of an analyte onto, or absorption of an analyte into, the material.

For example, U.S. Patent Application Publication 2006/0249402 to Snow et al. discloses a sensing device having a bottom electrode, a dielectric on the bottom electrode, a grid of nanoelectrodes on the dielectric, and a top electrode in electrical contact with the grid. The nanoelectrodes may be a network of carbon nanotubes. Such an arrangement is described by Snow et al. as being capable of exhibiting a capacitance change in the presence of a chemical analyte.

U.S. Patent Application Publication 2006/0237310 to Patel et al. discloses a device that is described as being able to detect various target analytes by adsorption or absorption of the analyte in a chemical sensing material such that an electrical property (e.g. capacitance, resistance, etc.) is altered in a manner detectable by circuitry associated with the sensing electrode pair coated with the chemical sensing materials.

U.S. Pat. No. 5,512,882 to Stetter and Maclay discloses a sensor whose impedance changes upon exposure to a vapor of a selected chemical substance. The sensor comprises a polymer whose physical structure is altered by the vapor (e.g., through expansion or disintegration). The sensor further comprises electrically conductive elements that are interspersed with the polymer. Changes can be measured by an impedance-measuring circuit.

U.S. Pat. No. 5,482,678 to Sittler discloses a sensor comprising a material which expands in the presence of an organic liquid, gas or vapor. The material is applied to a support surface such that upon expansion, the support deflects and changes the distance between two capacitor plates, thereby changing an electrical capacity between the plates.

U.S. Pat. No. 5,965,451 to Plog and Maunz discloses a gas sensor for selective detection of hydrocarbons, having a capacitive element and a gas-permeable sensitive layer as a dielectric. The sensitive layer is precious-metal-doped zeolite which has a regular crystalline structure made of primary pores whose diameter is on the order of the gas-kinetic diameter of the gas molecules to be detected.

SUMMARY

Applicant discloses a sensing element that is suitable for detecting or monitoring organic chemical analytes in an environment, for example in ambient atmosphere. Such a sensing element comprises an analyte-responsive dielectric material which is in proximity to first and second electrodes. In this context, an analyte-responsive dielectric material means a material that is capable of sorbing an organic chemical analyte, and that can exhibit a measurable change in an electrical property upon sorbing the organic analyte into the material. In one embodiment, the analyte-responsive dielectric material exhibits a change in dielectric constant upon sorbing the analyte, such that the sensing element comprises a capacitor and a change in capacitance of the sensing element can be observed.

In one embodiment, the analyte-responsive dielectric material is a microporous, hydrophobic material comprising an amorphous random covalent network comprising at least about 30% carbon atoms, and having a mean pore size of less than about 10 nm and a porosity of at least about 20%. Such a material may provide advantages in terms of high sensitivity to low levels of organic analytes, rapid response to organic analytes, and low sensitivity to water. Without being limited by theory or mechanism, the performance found in use of such a materials as an analyte-responsive dielectric materials may be due to any or all of several properties: hydrophobicity, an optimum amount of porosity, a microporous pore volume that encompasses an optimum pore size range, and the ability of the amorphous random covalent network to be deposited by plasma deposition so as to form an analyte-responsive dielectric layer.

In one aspect, herein is disclosed a sensor for sensing an organic chemical analyte, comprising: a sensing element that comprises a first electrode and a second electrode and a microporous, hydrophobic, analyte-responsive dielectric material disposed at least in proximity to the first and second electrodes, wherein the microporous, hydrophobic analyte-responsive dielectric material comprises an amorphous random covalent network comprising at least about 30% carbon, and having a mean pore size of less than about 10 nm and a porosity of at least about 20%; and, an operating circuit in electrical communication with the first and second electrodes, wherein the operating circuit is capable of applying a voltage to the first and second electrodes and is capable of detecting a change in an electrical property of the sensing element. In one embodiment, the amorphous random covalent network comprises at least about 30% carbon and further comprises silicon, oxygen, and hydrogen. In an alternative embodiment, the amorphous random covalent network comprises essentially 100% carbon.

In another aspect, herein is disclosed a method of sensing organic chemical analytes, comprising: providing a sensor that comprises a sensing element that comprises a first electrode and a second electrode and a microporous, hydrophobic, analyte-responsive dielectric material disposed at least in proximity to the first and second electrodes, wherein the microporous, hydrophobic analyte-responsive dielectric material comprises an amorphous random covalent network comprising at least about 30% carbon, and having a mean pore size of less than about 10 nm and a porosity of at least about 20%; and, an operating circuit in electrical communication with the first and second electrodes, wherein the operating circuit is capable of applying a voltage to the first and second electrodes and is capable of detecting a change in an electrical property of the sensing element; exposing the sensing element to an environment potentially containing one or more organic chemical analytes; applying a voltage to the first and second electrodes; and, monitoring an electrical property of the sensing element. In one embodiment, the amorphous random covalent network comprises at least about 30% carbon and further comprises silicon, oxygen, and hydrogen. In an alternative embodiment, the amorphous random covalent network comprises essentially 100% carbon.

In another aspect, herein is disclosed a method of making an organic chemical analyte sensing element, the method comprising: providing a substrate with a conductive layer; forming a plasma from a gas mixture comprising an organosilane, oxygen, and a hydrocarbon; exposing the substrate with conductive layer thereupon to the plasma such that an amorphous random covalent network layer comprising at least about 30% carbon, and further comprising silicon, hydrogen, and oxygen, is formed atop the conductive layer; heating the amorphous random covalent network to form an analyte-responsive dielectric layer that comprises a microporous, hydrophobic, amorphous random covalent network having a mean pore size of less than about 10 nm and a porosity of at least about 20%; and, depositing a second conductive layer atop the analyte-responsive dielectric layer.

In yet another aspect, herein is disclosed a method of making an organic chemical analyte sensing element, comprising, providing a substrate with first and second conductive electrodes that are in an interdigitated configuration with spaces in between; forming a plasma from a gas mixture comprising an organosilane, oxygen, and a hydrocarbon; exposing the substrate with conductive electrodes thereupon to the plasma such that an amorphous random covalent network layer comprising at least about 30% carbon, and further comprising silicon, hydrogen, and oxygen, is formed at least in the spaces in between the interdigitated electrodes; heating the amorphous random covalent network to form an analyte-responsive dielectric layer that comprises a microporous, hydrophobic, amorphous random covalent network having a mean pore size of less than about 10 nm and a porosity of at least about 20%.

These and other aspects of the invention will be apparent from the detailed description below. In no event, however, should the above summaries be construed as limitations on the claimed subject matter, which subject matter is defined solely by the attached claims, as may be amended during prosecution.

Like reference symbols in the various figures indicate like elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings.

DETAILED DESCRIPTION

Although terms such as "top", bottom", "upper", lower", "front" and "back", and "first" and "second" may be used in this disclosure, it should be understood that those terms are used in their relative sense only.

Sensing Element

Figure 1:
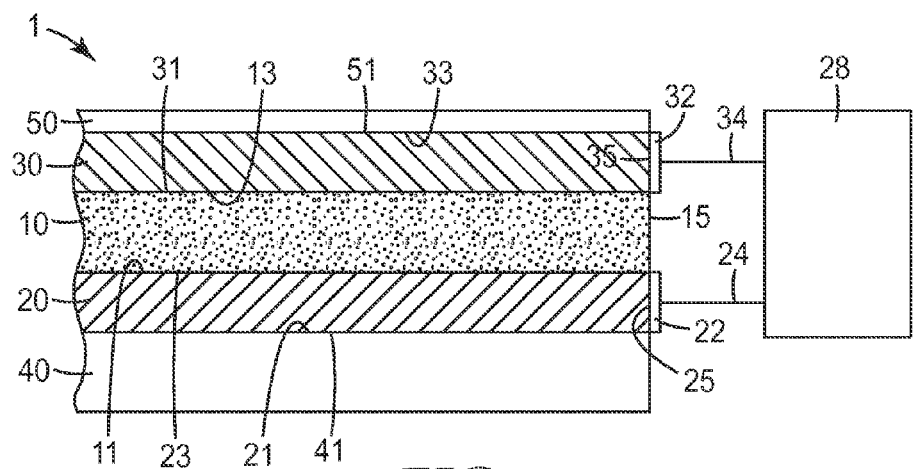
FIG. 1 is a side view of an exemplary sensing element in a parallel-plate configuration.
Figure 2:
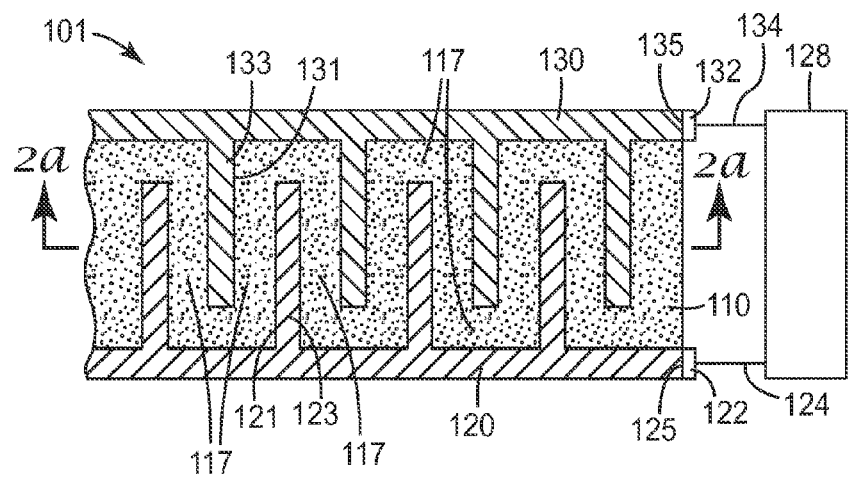
FIG. 2 is a top view of an exemplary sensing element in an interdigitated configuration.

With reference to FIGS. 1 and 2, herein is disclosed a sensing element 1/101 that comprises at least an analyte-responsive dielectric layer 10/110 in proximity to a first electrode 20/120 and a second electrode 30/130. These components, and features and properties thereof, as well as other optional components and the features and properties thereof, will be discussed in turn. These discussions will refer to both FIG. 1, which depicts an exemplary sensing element based on the general configuration of a parallel plate capacitor, and FIGS. 2, 2a, and 3, which depict exemplary sensing elements based on the general configuration of an interdigitated capacitor. For clarity, the various components have been given different reference numbers (generally, incremented by 100) in the Figures. depicting the different general configurations. However, it should be understood that the structure, composition and properties of the various components, may be applicable to sensing elements of any capacitive design, unless otherwise stated.

The sensing element 1/101 is configured such that the analyte-responsive dielectric layer 10/110 is in sufficiently close proximity to the first electrode 20/120 and the second electrode 30/130 that the analyte-responsive dielectric material present in the layer will be capable of interacting with an electric field that is established by the electrodes. In operation of sensing element 1/101, analyte-responsive dielectric layer 10/110 exhibits a change in an electrical property upon sorbing one or more analytes. In one embodiment, the electrical property is capacitance or a capacitance-related property as described below. Such a change in a capacitance-related property can be measured by imparting a charge differential between the first electrode 20/120 and the second electrode 30/130 (e.g., by imparting a voltage differential to the electrodes) and monitoring the property of the sensing element in response to the presence of the analyte. Such monitoring can be done by the use of an operating circuit 28/128, as described later herein.

The terms "capacitance" and "capacitance-related property" encompass any electrical property and the measurement thereof that is in general associated with the imparting of an electrical charge (whether static or time variant) and the monitoring of an electrical property during and/or after the imparting of the charge. Such properties include not only capacitance, but also impedance, admittance, resistance, conductance, etc., and may be measured according to various methods known in the art.

Analyte-Responsive Dielectric Layer

The analyte-responsive dielectric layer 10/110 (the term "layer" being used generically and encompassing any physical configuration) comprises at least in part an analyte-responsive dielectric material. In this context, the term "analyte-responsive dielectric material" means a material that is capable of sorbing an organic chemical analyte, and that can exhibit a measurable change in some electrical property of the material upon sorbing the organic analyte into the material.

Plasma Deposition

In one embodiment, the analyte-responsive dielectric material comprises an amorphous random covalent network of atoms. Such an amorphous random covalent network can be formed by plasma deposition. In this context, "plasma" means an at least partially ionized gaseous or fluid state of matter containing reactive species (e.g. electrons, ions, neutral molecules, free radicals, other excited state atoms and molecules, etc.).

In various embodiments, the amorphous random covalent network comprises at least about 20%, at least about 30%, or at least about 40% carbon atoms (these percentages represent a number average; e.g. a network comprising 30% carbon atoms, will on average, possess 30 atoms of carbon for every 100 total atoms).

In a particular embodiment, the amorphous random covalent network is comprised of essentially 100% carbon (except for such trace amounts of other atoms as may occur, for example, due to the presence of trace amounts of other gases in the plasma reactor). Such a structure can be made by, for example, forming a carbon-hydrogen amorphous random covalent network and then performing a thermal treatment as explained below.

In other embodiments, the non-carbon portion of the amorphous random covalent network can comprise atoms chosen from the group including silicon, oxygen, hydrogen, and/or nitrogen, alone or in combination. In further embodiments, the non-carbon portion of the amorphous random covalent network can also comprise atoms chosen from the group including halogens (fluorine, chlorine, etc.).

In one embodiment, the amorphous random covalent network comprises silicon atoms, carbon atoms, hydrogen atoms, and oxygen atoms, and is made via deposition from a plasma that comprises a mixture of silicon, carbon, oxygen and hydrogen atoms or molecules, using methods described in detail below. In a specific embodiment, the plasma is fed with a mixture of organosilane, oxygen and hydrocarbon.

Such an amorphous random covalent network typically comprises a continuous matrix. Such a matrix is herein defined as an assembly (e.g. a coating, layer, etc.) in which the solid portion of the material is continuously interconnected by virtue of covalent bonds (irrespective of the presence of porosity as described in detail below). That is, a continuous matrix is distinguishable from an assembly that comprises an aggregation of particles (e.g. zeolites, activated carbons, carbon nanotubes, etc.). For example, a plasma-deposited layer or coating (e.g. an amorphous random covalent network) will comprise a continuous matrix, even if the coating itself is applied in a patterned manner and/or comprises microporous pores.

In various embodiments, organosilanes that may be used for plasma deposition include, but are not limited to, tetramethylsilane, methylsilane, dimethylsilane, trimethylsilane, ethylsilane, tetraethylorthosilicate (TEOS), tetramethylcyclotetrasiloxane (TMCTS), disilanomethane, bis(methylsilano)methane, 1,2-disilanoethane, 1,2-bis(methylsilano)ethane, 2,2-disilanopropane, diethylsilane, diethylmethylsilane, propylsilane, vinylmethylsilane, divinyldimethylsilane, 1,1,2,2-tetramethyldisilane, hexamethyldisilane, 1,1,2,2,3,3-hexamethyltrisilane, 1,1,2,3,3-pentamethyltrisilane, dimethyldisilanoethane, dimethyldisilanopropane, tetramethyldisilanoethane, tetramethyldisilanopropane, and the like, or combinations of two or more of the foregoing.

In various embodiments, hydrocarbons that may be used for plasma deposition include, but are not limited to, straight or branched chain alkanes, alkenes, alkynes, and cyclic hydrocarbons having two to ten carbon atoms. Suitable hydrocarbons include (C1-C10) alkanes or (C1-C10) alkynes, such as for example, methane, ethane, propane, butane, benzene, cyclohexane, toluene, ethylene, propylene, acetylene, and butadiene.

In one embodiment, molecular oxygen ($O_2$) is used in the plasma generation and deposition process. This may result in oxygen atoms being present in a more randomly distributed manner throughout the amorphous random covalent network, compared to providing the oxygen only as part of larger molecules (e.g. molecules comprising Si—O groups, C—O groups, etc.), in which case the oxygen atoms may be present in the amorphous random covalent network preferentially close to Si, C, etc.

Any suitable plasma reactor can be used to form the amorphous covalent network thin film described herein. One suitable plasma reactor apparatus provides a reaction chamber having a capacitively-coupled system with at least one electrode powered by a radiofrequency (RF) source and at least one grounded electrode. One suitable reaction chamber is evacuable and is capable of maintaining conditions that produce plasma treatment. That is, the chamber provides an environment which allows for the control of, among other things, pressure, the flow of various inert and reactive gases, voltage supplied to the powered electrode, strength of the electric field across the ion sheath, formation of a plasma containing reactive species, intensity of ion bombardment, and rate of deposition of the amorphous covalent network from the reactive species. In one apparatus, aluminum is the chamber material because it has a low sputter yield, which means that very little contamination occurs from the chamber surfaces. However, other suitable materials, such as graphite, copper, glass or stainless steel, may be used.

In order to use the plasma deposition process to form an amorphous random covalent network atop a substrate, the substrate is typically placed in, or passed through, the evacuable reaction chamber. In some embodiments, a multiplicity of amorphous covalent network films may be simultaneously formed atop a multiplicity of substrates during the process.

Plasma, created from the gas within the chamber, is generated and sustained by supplying power (for example, from an RF generator operating at a frequency in the range of 0.001 to 100 MHz) to at least one electrode. The electrode system may be symmetric or asymmetric. In some plasma apparatus, electrode surface area ratios between grounded and powered electrodes are from 2:1 to 4:1, or from 3:1 to 4:1. The powered electrode may be cooled, e.g., with water. For discrete planar articles, plasma deposition can be achieved, for example, by placing the articles in direct contact with the smaller electrode of an asymmetric electrode configuration. This allows the article to act as an electrode due to capacitive coupling between the powered electrode and the article.

The RF power source provides power at a typical frequency in the range of 0.01 to 50 MHz, or 13.56 MHz or any whole number (e.g., 1, 2, or 3) multiple thereof. The RF power source can be an RF generator such as a 13.56 MHz oscillator. To obtain efficient power coupling (i.e., wherein the reflected power is a small fraction of the incident power), the power source may be connected to the electrode via a network that acts to match the impedance of the power supply with that of the transmission line (which is usually 50 ohms reactive) so as to effectively transmit RF power through a coaxial transmission line. One type of matching network, which includes two variable capacitors and an inductor, is available under the designation AMN 3000 from Plasmatherm of St. Petersburg, Fla. Traditional methods of power coupling involve the use of a blocking capacitor in the impedance matching network between the powered electrode and the power supply. This blocking capacitor prevents the DC bias voltage from being shunted out to the rest of the electrical circuitry. Instead, the DC bias voltage is shunted out in a grounded electrode. While the acceptable frequency range from the RF power source may be high enough to form a large negative DC self bias on the smaller electrode, it should not be so high that it creates standing waves in the resulting plasma, which is inefficient for plasma treatment.

Thermal Treatment/Microporous Structure

In one embodiment, the plasma-deposited amorphous random covalent network is subjected to thermal treatment to drive out hydrogen and/or hydrocarbon from the network so as to form a microporous structure. In this context, "microporous" means that the material has a significant amount of internal, interconnected pore volume, with the mean pore size (as characterized, for example, by sorption isotherm procedures) being less than about 100 nm. Thus, if present, molecules of organic analyte are able to penetrate the internal pore volume of the material and take up residence in the pores. The presence of such analyte in the internal pores can alter the dielectric properties of the material such that a change in the dielectric constant (or any other suitable electrical property) can be observed.

Without being limited by theory or mechanism, applicant considers that the disclosed sensing element 1/101, relying on a microporous dielectric material, may have advantageous properties with regard to the sensing of an organic analyte, in that a measurable change in an electrical property of the dielectric material may be caused by the presence of the analyte molecules in the pores. Thus, it may be possible to detect the analyte without the analyte molecules being required to be solubilized in the dielectric material itself to a sufficient extent to cause a change in a property of the dielectric material such as swelling and/or expansion (although such a phenomenon may also occur and may also contribute to a measurable electrical response). Such a microporous nature of the analyte-responsive dielectric material may contribute to increased sensitivity of the dielectric material to small amounts of organic analyte.

In various embodiments, the analyte-responsive dielectric material has a porosity of at least about 20%, at least about 30%, or at least about 40% (as characterized, for example, by sorption isotherm techniques, such as those using, for example, instruments available under the trade mark Autosorb from Quantachrome Instruments of Boynton Beach, Fla.). Such porosity can provide good response to low levels of organic chemical analytes. However, the analyte-responsive dielectric material should not have such a high pore volume that it is difficult to avoid electrical shorting or arcing between the first electrode 20/120 and the second electrode 30/130. Thus, in various embodiments, the analyte-responsive dielectric material comprises a porosity of at most about 90%, at most about 70% or at most about 50%.

Again without being limited by theory or mechanism, the size and distribution of the internal pores may be such that at least some of the organic analyte molecules in at least some of the pores may form a more highly condensed state (e.g. a quasi-liquid state) than they would otherwise be in (e.g., than they would be in the environment in which the analyte is monitored). This may result in analyte molecules collecting in the internal pores in larger numbers and/or at a higher concentration than they are present in the environment being monitored; in addition, or instead, the analyte molecules in this state may exhibit a higher dielectric constant (relative permittivity) than in an uncondensed vaporous or gaseous state. Thus, a sensing element based on a microporous analyte-responsive dielectric material with appropriately chosen size and distribution of pores may exhibit superior sensitivity to small quantities of organic analyte. In various embodiments, the analyte-responsive dielectric material comprises a mean pore size of less about 50 nm, less than about 20 nm, less than about 10 nm, or less than about 5 nm. In various embodiments, the analyte-responsive dielectric material comprises a mean pore size of greater than about 0.3 nm, greater than about 0.5 nm, or greater than about 1.0 nm.

In one embodiment, the analyte-responsive dielectric material is substantially free of pores greater than one μm in diameter.

The analyte-responsive dielectric material comprising an amorphous random covalent network can be thermally treated so as to form the above-discussed microporous structure. Specific heating conditions can be selected so as to modify other properties of the material. For example, a more hydrophobic structure can be formed by heating the amorphous random covalent network in an inert (or reducing) atmosphere and/or at a pressure less than atmospheric. Such a hydrophobic material typically will not sorb liquid water to an extent that the material swells significantly or otherwise exhibits a significant change in a physical property, and may be useful in providing an organic analyte sensing element that is relatively insensitive to the presence of water. Typical heating methods that can be used to produce suitable hydrophobic, microporous, analyte-responsive dielectric materials include, for example, heating of the material under vacuum in a vacuum oven at 450 degrees Centigrade for one hour.

In the particular case of the deposition of an amorphous random covalent network comprising only carbon and hydrogen (e.g., made from a plasma comprising a hydrocarbon), a suitable thermal treatment may be used to remove substantially all of the hydrogen so as to form a microporous material comprising essentially 100% carbon.

The analyte-responsive dielectric layer 10/110 comprising a plasma-deposited, microporous, analyte-responsive dielectric material can have any desired overall thickness. In various embodiments, layer 10/110 has an overall thickness of less than about 2000 nm, or less than about 1000 nm. In other embodiments, layer 10/110 has an overall thickness of more than about 50 nm, more than about 100 nm, or more than about 200 nm. In one embodiment, layer 10/110 has a thickness that is substantially the same throughout the length and breadth of the layer.

In one embodiment, the plasma-deposited layer is deposited atop a layer of conductive material that is suitable to serve as one electrode of a capacitive sensing element (as discussed in detail below). In various embodiments, an additional layer or layers of a material that is not an analyte-responsive dielectric material may be provided in proximity to the analyte-responsive dielectric layer. Such a layer or layers may be provided for any of a variety of reasons, e.g. as a protective layer, as a tie layer to improve adhesion, and so on. In additional embodiments, the plasma deposited material may be patterned. Suitable methods of forming the material in a patterned configuration include, but are not limited to, spatially controlling the deposition conditions of the material to vary the thickness or density of the material. For example, a mask can be placed between the deposition source and the substrate such that the thickness of the deposited material varies from a first location to a second location on an upper surface.

In various embodiments, multiple individual layers of analyte-responsive dielectric material can be used. For example, multiple layers of plasma-deposited analyte-responsive dielectric material can be used. Alternatively, one or more layers of some other analyte-responsive dielectric material can be used in addition to a layer of plasma-deposited analyte-responsive dielectric material. The various layers of analyte-responsive dielectric material can be in direct contact with each other; or, they can be separated by a layer or layers present for some other purpose (e.g., passivation layers, tie layers, as described herein).

Electrodes

With reference to FIGS. 1 and 2, the first electrode 20/120 and second electrode 30/130 can comprise any suitable conductive material. Combinations of different materials (conductive and/or nonconductive) can be used, as different layers or as a mixture, as long as sufficient overall conductivity is provided (e.g., the electrode material comprises a constant resistivity of less than about $10^{-2}$ ohms-meter). Examples of materials that can be used to make the first electrode and/or second electrode include, but are not limited to, organic materials, inorganic materials, metals, alloys, and various mixtures and composites comprising any or all of these materials. In certain embodiments, coated (for example, vapor coated, sputter coated, etc.) metals or metal oxides, or combinations thereof, may be used. Suitable conductive materials include for example aluminum, tin, indium-tin oxide, gold, silver, platinum, palladium, copper, nickel, titanium, chromium and the like. In one embodiment, both electrodes comprise the same material; in an alternative embodiment, the first and second electrodes comprise different materials, In various embodiments either or both of the electrodes can be permeable to an organic analyte. Such electrode permeability may be particularly useful in the case of a sensing element which is configured in the general manner of a parallel-plate capacitor as shown in FIG. 1. In such a case, if second electrode 30 is permeable, an organic analyte can enter analyte-responsive dielectric layer 10 through major surface 13, rather than having to enter the analyte-responsive dielectric layer 10 by way of edge 15, which might be a slower process. Likewise, if first electrode 20 is permeable, an organic analyte may be able to enter analyte-responsive dielectric layer 10 through major surface 11 (however, if backing 40 is not permeable to the analyte, it may not be useful to provide first electrode 20 in a permeable configuration).

In various embodiments, an electrode can be analyte-permeable by virtue of being discontinuous. In this context, the term discontinuous does not imply that the electrode comprises units (spots, islands, etc.) that are not in electrical contact with each other. Rather, discontinuous means that within the overall boundaries of the electrode, some areas do not contain conductive material. Such a discontinuous electrode may be microscopically discontinuous. For example, an electrode can be formed by the deposition (e.g., by coating, ink jet printing, etc.) of a sol comprising particles (e.g. nanoparticles) of a conductive material. (Typical sols may be comprised of silver, gold, platinum, palladium or other metallic material.). In such a case, the electrode may comprise conductive particles that are in sufficient contact to ensure that the electrode is conductive, but with sufficient spaces in between the particles to render the electrode permeable to an organic analyte. In some embodiments, heating (e.g. sintering) the conductive material (e.g., at a temperature of from about 100 C to about 250 C, for a period of from about 10 min to about 2 hr) may enhance contact between the particles so as to improve conductivity while still maintaining vapor permeability. In other embodiments, an electrode can comprise a macroscopically discontinuous structure. For example, if a conductive material comprises vapor coated metal (which is typically impermeable), the conductive metal can be deposited in a pattern (for example, in a grid pattern, or in a "comb" pattern as disclosed in Example 1) rather than as a continuous layer.

With reference to FIGS. 1 and 2, an electrically accessible area 25/125 of first electrode 20/120, and an electrically accessible area 35/135 of second electrode 30/130, are provided such that it is possible to connect an operating circuit 28/128 to the sensing element via these areas. Such electrically accessible areas can be provided in any convenient location. For example, such electrically accessible areas are shown on an edge of the electrodes in the exemplary illustrations of FIGS. 1 and 2, and are shown on a major surface (123 and 133) of the electrodes in the exemplary illustration of FIG. 3. In one embodiment, a connecting device (e.g. a contact pad or tab) 22/122 is positioned in contact with (e.g. attached to) the accessible area of the first electrode 20, such that electrical connection can be made (for example via attachment of wires 24/124) between sensing element 1/101 and an operating circuit 28/128. A similar connecting device 32/132 can be likewise positioned in contact with the accessible area of the second electrode 30.

Exemplary Sensing Elements and Methods of Making Parallel-Plate Configuration

In one embodiment, a sensing element 1 can be produced which is configured in the general manner of a parallel-plate capacitor as shown in an exemplary manner in the cross sectional view of FIG. 1. In such a configuration, the sensing element comprises two generally planar, parallel, opposing electrodes, with the analyte-responsive dielectric layer being present in between the electrodes and preventing direct electrical contact between the two electrodes.

In an exemplary process for making such a sensing element, a backing 40 is provided (which may be a continuous slab, layer or film of material) that is in proximity to at least one of the electrodes and that may serve to provide physical strength and integrity to the finished sensing element. Any suitable material may be used, including glass, ceramic, plastic, etc. In large scale production, a polymeric film (e.g. polyester, polyimide, etc.) may be used. In some embodiments, the backing is an analyte-permeable material (for example, silicone rubber, a porous membrane, etc.).

In one embodiment, a conductive layer that serves as first electrode 20 is provided on backing 40. The conductive layer may comprise any of the materials mentioned above, including blends or mixtures of conductive and nonconductive materials, and may be deposited by any suitable method, including but not limited to spin coating, dip coating, solution die coating, screen printing, transfer coating, sputter-coating, physical vapor deposition, chemical vapor deposition, or a combination of two or more of such methods. In an alternate embodiment, the conductive layer may be provided by placing a premade film (e.g. a metal foil, conductive tape, etc.) atop backing 40. This first electrode 20 may be provided as a continuous layer or as a discontinuous layer, as previously described.

In one embodiment, the conductive layer is provided such that a first surface 21 of electrode 20 is in proximity to, and/or in contact with, at least a portion of the first surface 41 of backing 40. In an alternative embodiment, an optional layer is present between at least a part of first surface 21 of electrode 20, and first surface 41 of backing 40. Such an optional layer may be used for any purpose (such as improving the bond between first electrode 20 and backing 40), as long as the layer does not interfere with the functioning of the sensing element 1.

In producing sensing element 1, an analyte-responsive dielectric layer 10 is also provided. In one embodiment, the analyte-responsive dielectric layer 10 is provided such that first major surface 11 of layer 10 is in direct contact with at least a portion of the second surface 23 of first electrode 20 (leaving at least a portion of first electrode 20 accessible for connection to an operating circuit).

In one embodiment, the analyte-responsive dielectric material is placed in proximity to the first electrode by a plasma deposition process such as that described in detail above. In this case, the substrate and first electrode (upon which the analyte-responsive dielectric material is deposited) should be such that they survive the conditions under which the plasma is applied.

In another embodiment, the analyte-responsive dielectric layer can be provided by plasma deposition of analyte-responsive dielectric material onto a carrier substrate which is then placed atop the first electrode. In an alternative embodiment, analyte-responsive dielectric material can be plasma deposited onto a temporary carrier, after which the analyte-responsive dielectric material can be removed from the carrier and formed into a powder, which can then be deposited onto the first electrode.

In various embodiments, a second electrode 30 can be formed by placing a second conductive layer in proximity to the analyte-responsive dielectric layer 10. The second electrode 30 may comprise conductive materials as described above, and may be deposited according to methods described above. In certain embodiments (particularly in the case in which backing 40 is impermeable to an analyte), second electrode 30 may comprise a discontinuous structure (again as previously described) so as to be permeable to an organic analyte.

With reference to FIG. 1, an optional protective cover or barrier layer 50 can be provided in proximity to at least one of the electrodes. In one embodiment, cover layer 50 is placed atop second electrode 30 (leaving an area of second electrode 30 accessible for electrical contact). Any such cover layer 50 should not significantly interfere with the functioning of sensing element 1. For example, if the sensing element is configured such that an analyte of interest must pass through cover layer 50 in order to reach the analyte-responsive dielectric layer 10, the cover layer should be sufficiently permeable to the analyte.

Cover layer 50 may be deposited by any method known in the art, including coating (e.g. spin coating, dip coating, solvent coating, vapor coating, transfer coating, screen printing, flexographic printing, and the like). In an alternate embodiment, cover layer 50 can comprise a premade layer (e.g. a film or tape) that is placed upon second electrode 30. In one embodiment, cover layer 50 is provided such that first surface 51 of cover layer 50 is in direct contact with at least a portion of second surface 33 of second electrode 30. The second surface of the cover layer may be the outermost surface of the sensing element, or may itself receive additional coatings or layers if desired.

In one embodiment, the analyte-responsive dielectric layer is thermally treated (for example, exposed to a temperature of 450° C. for one hour) so as to increase the porosity and/or increase the hydrophobicity of the amorphous random covalent network, at any suitable point in the above process. For example, the substrate/first electrode/analyte-responsive dielectric layer combination may be thermally treated, after which the second electrode (and any optional cover layer) is formed. Or, the entire substrate/first electrode/analyte-responsive dielectric layer/second electrode combination may be formed and then heat treated. Any components (e.g. substrate, electrodes, optional tie layers, optional cover layers, electrical connecting devices, etc.) that are present during the thermal treatment must be chosen so as to be able to survive the thermal treatment and still perform their desired function in the sensing element.

In one embodiment, the second surface 23 of first electrode 20 and first major surface 11 of the analyte-responsive dielectric layer 10 are in direct contact, with no interposing layer(s) therebetween. Likewise in one embodiment, the first surface 31 of second electrode 30 and second major surface 13 of the analyte-responsive dielectric layer 10 are in direct contact, with no interposing layer(s) therebetween. Such embodiments are pictured in FIG. 1. However, it is also contemplated that other, optional layers may be present between the first electrode 20 and the analyte-responsive dielectric layer 10, and/or between the second electrode 30 and the analyte-responsive dielectric layer 10. In such a case, either or both of the electrodes may not be in direct contact with some or all of a surface of the analyte-responsive dielectric material. For example, a tie layer or layers may be used to improve the bonding between an electrode and the analyte-responsive dielectric layer. Or, a passivation layer or layers (for example, a layer of silicon dioxide) may be placed in between a surface of the analyte-responsive dielectric layer and an electrode surface, in order to minimize the possibility of arcing between the electrodes. In some embodiments, multiple such optional layers may be used; alternatively a single layer may serve multiple functions. Any such optional layer or layers such as the aforementioned tie layers, passivation layers, protective layers, cover layers, etc., may be used, for whatever purpose, as long as they do not significantly interfere with the desired functioning of the sensing element. For example, an optional layer should be sufficiently permeable to an analyte of interest if the sensing element is configured such that the analyte must pass through the optional layer in order to reach the analyte-responsive dielectric layer 10.

In general, the edges of the various layers can be aligned flush with each other (as depicted in the exemplary embodiment of FIG. 1). Alternatively, various layers may overlap other layers, and/or the edges of certain layers may be recessed relative to other layers.

In the deposition of the analyte-responsive dielectric material atop first electrode 20, an electrically accessible area 25 should be provided on first electrode 20, to enable electrical contact between the electrode and an operating circuit. Similarly, if a cover layer is placed atop second electrode 30, an electrically accessible area 35 should be similarly provided. Such electrically accessible areas can be provided in any convenient location. In one embodiment, a connecting device (e.g. a contact pad, tab, or the like) 22 may be placed in electrical contact with accessible area 25 of first electrode 20. Similarly, a connecting device 32 may be placed likewise in contact with accessible area 35 of second electrode 30.

Interdigitated Configuration

Figure 2A:
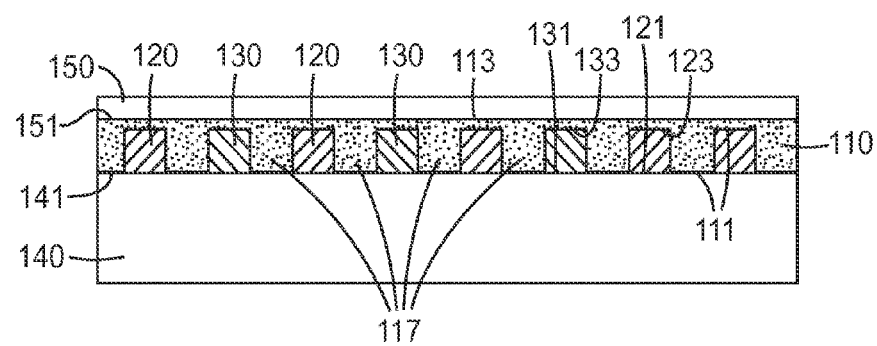
FIG. 2a is a cross sectional view of the exemplary sensing element of FIG. 2, taken along the line marked "2a" in FIG. 2.
Figure 3:
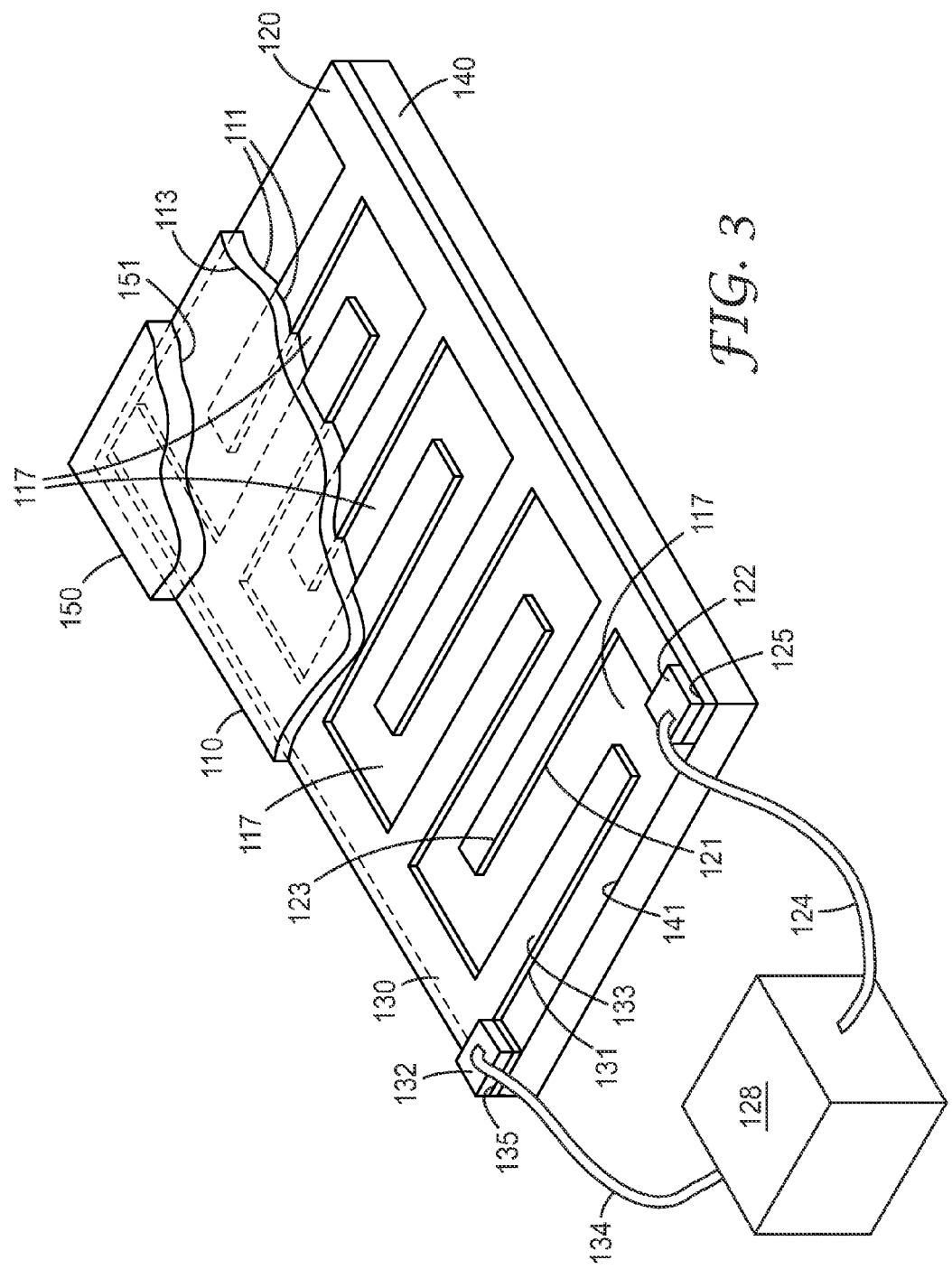
FIG. 3 is a perspective view of an exemplary sensing element in an interdigitated configuration.

In another embodiment, a sensing element can be produced that is configured in the general manner of an interdigitated capacitor. Exemplary embodiments of interdigitated sensing elements are shown in the top view of FIG. 2, in the cross-sectional view of FIG. 2a (taken along the line marked "2a" in FIG. 2), and in the perspective view of FIG. 3. In this context, the term interdigitated encompasses any arrangement comprising at least two electrodes present in an interdigitated configuration. Such configurations include interdigitated comb patterns (such as depicted in FIGS. 2, 2a and 3), as well as interdigitated spiral or serpentine patterns as are well known in the art. All of these designs have the common characteristic that (at least) two electrodes are provided in a largely coplanar interdigitated arrangement with an analyte-responsive dielectric layer present in proximity to the electrodes such that when an electric field is established between the electrodes, an analyte-responsive dielectric material contained in the layer is capable of interacting with the electric field. The analyte-responsive dielectric layer/material may be provided between the electrodes (i.e. in the plane of the two electrodes and interposed in the linear path between any two closest points of approach of the first and second electrodes).

Alternatively, the analyte-responsive dielectric layer/material may be provided such that, while not coplanar with the electrodes, the analyte-responsive dielectric material is exposed at least to the fringing electric field that is established between adjacent sections of the two electrodes. In still another alternate embodiment, the analyte-responsive dielectric layer may be provided in both locations.

Interdigitated electrodes can be provided by the deposition of conductive material in two interdigitated patterns by any of the methods (e.g. masked vapor deposition, screen-printing, ink-jet printing) that are well known for patterned deposition of materials. The particular geometric/dimensional properties of the electrode patterns (spacing, height, length etc.) may be designed as desired.

In one embodiment, interdigitated electrodes are provided on a backing 140 which may be comprised of materials described above. First electrode 120 and second electrode 130 are typically provided on the same backing 140. In one embodiment (shown in FIGS. 2, 2a and 3), first surface 121 of first electrode 120, and first surface 131 of second electrode 130, are both in direct contact with at least some portion of the first surface 141 of backing 140. In an alternative embodiment (not pictured), an optional layer or layers can be present between the electrode 120 and/or 130 and the backing 140, similar to the optional layers described above, and subject to the same issues and constraints.

As illustrated in the exemplary embodiments of FIGS. 2, 2a, and 3, the patterned deposition of first electrode 120 and second electrode 130 may leave an area of surface 141 of backing 140, (or, of the surface of any optional layer thereupon) exposed. An analyte-responsive dielectric layer can then be plasma-deposited onto backing 140, via similar methods to those described above with reference to sensing elements of a parallel-plate type. (Again, the substrate and/or electrodes should be selected and designed such that they survive the plasma deposition process.) The deposited analyte-responsive dielectric material will thus fill the spaces between the two electrodes (e.g. spaces 117 depicted in FIGS. 2, 2a, and 3). Thus, in this embodiment a first surface 111 of the analyte-responsive dielectric layer 110 will be in direct contact with at least a portion of surface 141 of backing 140. The deposition process may also cause the analyte-responsive dielectric layer 110 to cover, and be in contact with, second surface 123 of the first electrode, and second surface 133 of the second electrode, as depicted in FIGS. 2a and 3 (unless the deposition is performed selectively, e.g. with one or both of the electrodes masked). Thus, in various embodiments, the first surface 111 of analyte-responsive dielectric layer 110 is in direct contact with second surface 123 of first electrode 120, and/or with second surface 133 of second electrode 130.

In alternative embodiments, an optional layer (not shown in FIGS. 2, 2a or 3) may be provided atop the second surface 123 of first electrode 120, and/or atop the second surface 133 of first electrode 130. In this embodiment, direct contact between first surface 111 of analyte-responsive dielectric layer 110 and second surface 123 of first electrode 120, and/or second surface 133 of second electrode 130, may not occur. Such an optional layer may serve similar purposes (protective, etc.) to those described earlier. However, in an interdigitated type sensing element, an optional layer atop one or both electrodes may not necessarily need to be permeable to the analyte since the analyte may not need to penetrate through the an optional layer to reach areas 117 of the analyte-responsive dielectric layer 110.

In one embodiment, an optional cover layer 150 (which may serve as a protective layer, insulating layer, decorative layer, etc.) may be deposited atop the second surface 113 of the analyte-responsive dielectric layer 110. Any such cover layer should not significantly interfere with the functioning of the sensing element (e.g., it should be sufficiently permeable to an analyte of interest). This cover layer may comprise a coating deposited by any known coating process (e.g. spin coating, dip coating, solvent coating, vapor coating, transfer coating, screen printing, flexographic printing, and the like). In an alternate embodiment, cover layer 150 can comprise a premade layer (e.g. a film or tape) that is placed atop second surface 113 of layer 110.

In one embodiment, the analyte-responsive dielectric layer is thermally treated so as to increase the porosity and/or increase the hydrophobicity of the amorphous random covalent network. Any components (e.g. substrate, electrodes, optional tie layer, optional cover layers, electrical connecting devices, etc.) that are present during the thermal treatment should be chosen so as to be able to survive the thermal treatment and still perform their desired function in the sensing element.

In the deposition of the analyte-responsive dielectric material (and of any optional cover layer), an electrically accessible area 125 should be provided on first electrode 120, and an accessible area 135 on second electrode 130, to allow electrical contact between each electrode and an operating circuit. Such electrically accessible areas can be provided in any convenient location. For example, such electrically accessible areas 125 and 135 are shown on an edge of an electrode in the exemplary illustration of FIG. 2, and are shown on surfaces 123 and 133 of an electrode in the exemplary illustration of FIG. 3.

In one embodiment, a connecting device (e.g. a contact pad, tab, or the like) 122 may be placed in electrical contact with accessible area 125 of first electrode 120. Similarly, a connecting device 132 may be placed likewise in contact with accessible area 135 of second electrode 130.

Operating Circuit

Upon sorption of sufficient analyte by the analyte-responsive dielectric layer, a measurable change in an electrical property associated with the sensing element (including but not limited to, capacitance, impedance, admittance, current, or resistance) may occur. Such a detectable change may be detected by an operating circuit 28/128 that is in electrical communication with the first and second electrodes. In this context, "operating circuit" refers generally to an electrical apparatus that can be used to apply a voltage to the first electrode and the second electrode (thus imparting a charge differential to the electrodes), and/or to monitor an electrical property of the sensing element, wherein the electrical property may change in response to the presence of an organic analyte. In various embodiments, the operating circuit may monitor any or a combination of inductance, capacitance, voltage, resistance, conductance, current, impedance, phase angle, loss factor, or dissipation.

Such an operating circuit may comprise a single apparatus that both applies voltage to the electrodes, and monitors an electrical property. In an alternative embodiment, such an operating circuit may comprise two separate apparatuses, one to provide voltage, and one to monitor the signal. An operating circuit may be connected to first electrode 20/120 and to second electrode 30/130 by wires 24/124 and 34/134. In an alternative embodiment, an operating circuit may be provided in direct contact with the first and/or the second electrode, either via connecting devices 22/122 and 32/132, or by contacting some portion of the operating circuit directly to an electrically accessible area of each electrode. For example, an operating circuit can be provided that resides on a circuit board or a flexible circuit (either of which can also serve as backing 40/140). A first electrode can then be deposited directly onto circuit board/backing 40 such that it is in direct contact with a portion of the operating circuit.

An operating circuit 28/128 may include, for example, a power supply (which may comprise a battery or a hardwired power source; alternatively, power may be provided indirectly via, for example, charging of an RFID circuit that is built into the operating circuit). An operating circuit 28/128 may also include one or more microprocessors configured to control the charging of the electrodes and/or to monitor changes in one or more electrical properties of a charged sensing electrode pair. Also present may be analog-to-digital converters, memory devices for storing data derived from the sensing element, software for operating the sensing element, components that provide data logging and/or one- or two-way telemetry capability, and so on.

Analytes

A sensing element such as herein disclosed can be used to detect and/or monitor (whether qualitatively or quantitatively) the presence of an organic analyte or analytes. Such analytes can include, but are not limited to, hydrocarbons, fluorocarbons, alkanes, cycloalkanes, aromatic compounds, alcohols, ethers, esters, ketones, halocarbons, amines, organic acids, cyanates, nitrates, and nitriles, for example n-octane, cyclohexane, methyl ethyl ketone, acetone, ethyl acetate, carbon disulfide, carbon tetrachloride, benzene, styrene, toluene, xylenes, methyl chloroform, tetrahydrofuran, methanol, ethanol, isopropyl alcohol, n-butyl alcohol, t-butyl alcohol, 2-ethoxyethanol, acetic acid, 2-aminopyridine, ethylene glycol monomethyl ether, toluene-2,4-diisocyanate, nitromethane, and acetonitrile and the like. Analytes can be relatively nonpolar organic molecules or relatively polar organic molecules. Analytes can be so-called vapors; i.e. molecules that are capable of forming a solid or liquid under the ambient conditions of temperature and pressure that the analyte is experiencing (e.g. toluene, acetone, heptane, etc.). Analytes can be so-called gases; i.e. molecules that are not normally capable of forming a liquid or solid under ambient conditions (although such molecules may still comprise a more highly condensed state in the internal pores of the analyte-responsive dielectric material, as discussed above). Such gases may include methane, ethane, and the like. Mixtures of organic analyte molecules may in some circumstances be detected.

The invention is further illustrated by the following example.

Example

Plasma Reactor

The amorphous random covalent network layers were deposited by use of a planar radiofrequency (RF) plasma system. The system was pumped by a turbomolecular pump (Model TPH2000, Balzers) backed by a dry pumping station (EH1200 roots pump EH1200, Edwards; and iQDP80 dry mechanical pump, Edwards). The gas flow rates were controlled by digital flow controllers (MKS Corporation). RF power was delivered using a Model RF50S power supply (available from RF Power Products, Voorhees, N.J.), operating through a Model AMN3000 impedance matching network (available from Plasmatherm, St. Petersburg, Fla.).

Preparation of Sample 1

A cleaned piece of glass (2.5 cm by 2.5 cm) was coated with a continuous (unpatterned) coating of aluminum using a CHA Industries Mark-50 evaporator operated at a base pressure of $1 \times 10^{-5}$ torr and No. A-2049 aluminum pellets (99.995% purity, 6×6 mm, from Cerac Inc.). The aluminum coating was deposited at a rate of approximately 15 angstroms/second. The final thickness was approximately 100 nm. A diamond-tipped pen was used to score the aluminized glass approximately 5 mm from one edge, such that two aluminum-coated areas, not in electrical contact with each other, were provided. The larger area thus formed a first electrode, and the smaller (edge) area thus formed an area to which electrical contact could be made to a (subsequently applied) second electrode, as described below. The scored piece of aluminized glass was taped down to a 5 cm by 5 cm piece of glass for ease of handling. Masking material was positioned atop an edge portion of the smaller aluminum-coated area. Masking material was also positioned atop an edge portion of the larger aluminum-coated area.

The glass pieces were mounted onto a planar electrode (by taping with polyimide tape) in the above-described plasma reactor system. The chamber was closed and pumped down to a pressure of approximately 0.07 Pa. A gas mixture containing tetramethylsilane, 1,3-butadiene and oxygen was fed into the vacuum chamber at the flowrates listed below. Plasma was maintained under the conditions described below:

Flow rate of tetramethylsilane: 100 sccm (std cubic centimeters per minute)
Flow rate of 1,3-butadiene: 160 sccm
Flow rate of oxygen: 100 sccm
Process pressure: 37 mTorr (4.9 Pa)
Rf power: 75 Watts
Deposition time: 14 minutes.

This process resulted in an approximately 0.77 µm thick layer comprising an amorphous random covalent network material. The masking materials were then removed from the samples. The sample was then thermally treated in an evacuated vacuum oven at approximately 450° C. for one hour.

A patterned second electrode was inkjet printed on top of the plasma deposited material to complete the construction of this sample. In order to inkjet print the second electrode, a bitmap image (702 dots per inch) was created in Adobe Photoshop and then downloaded to an XY deposition system. The printhead used for depositing the silver was a Dimatix SX3-128 printhead with a 10 pL drop volume and 128 jets/orifices, the printhead assembly being approximately 6.5 cm long with 508 micron jet to jet spacing. The silver nanoparticle sol used to construct this electrode was obtained from Cabot under the designation AG-ID-G-100-S1. The sample was held securely during the inkjet printing process by use of a porous aluminum vacuum platen. Upon completion of printing, the sample was removed from the porous aluminum vacuum platen and placed on a Thermolyne hot plate for 10 minutes at 125° C.

The inkjet printed silver electrode comprised a comb pattern that consisted of a solid rectangle with lines extending from one edge. The rectangular portion of the printed electrode was positioned such that a portion of the rectangle was atop a portion of the smaller aluminum-coated area (such that electrical contact with the top electrode could be achieved by attaching a wire to the smaller aluminum-coated area), with the remainder of the second printed electrode being atop the plasma-deposited material. The lines on the electrode were designed to be approximately 8.3 mm long and approximately 250 microns wide. The gap between the lines was designed to be approximately 250 microns. (It should be noted that all of these dimensions were the nominal dimensions of the bitmap image and not the actual 'printed' dimensions).

This procedure provided a glass backing layer with a first electrode comprising continuous aluminum. Atop the aluminum electrode was an analyte-responsive dielectric layer comprising a plasma-deposited material, with a second electrode comprising a silver layer in a comb pattern residing atop the plasma-deposited layer.

Testing of Sample 1

Figure 4:
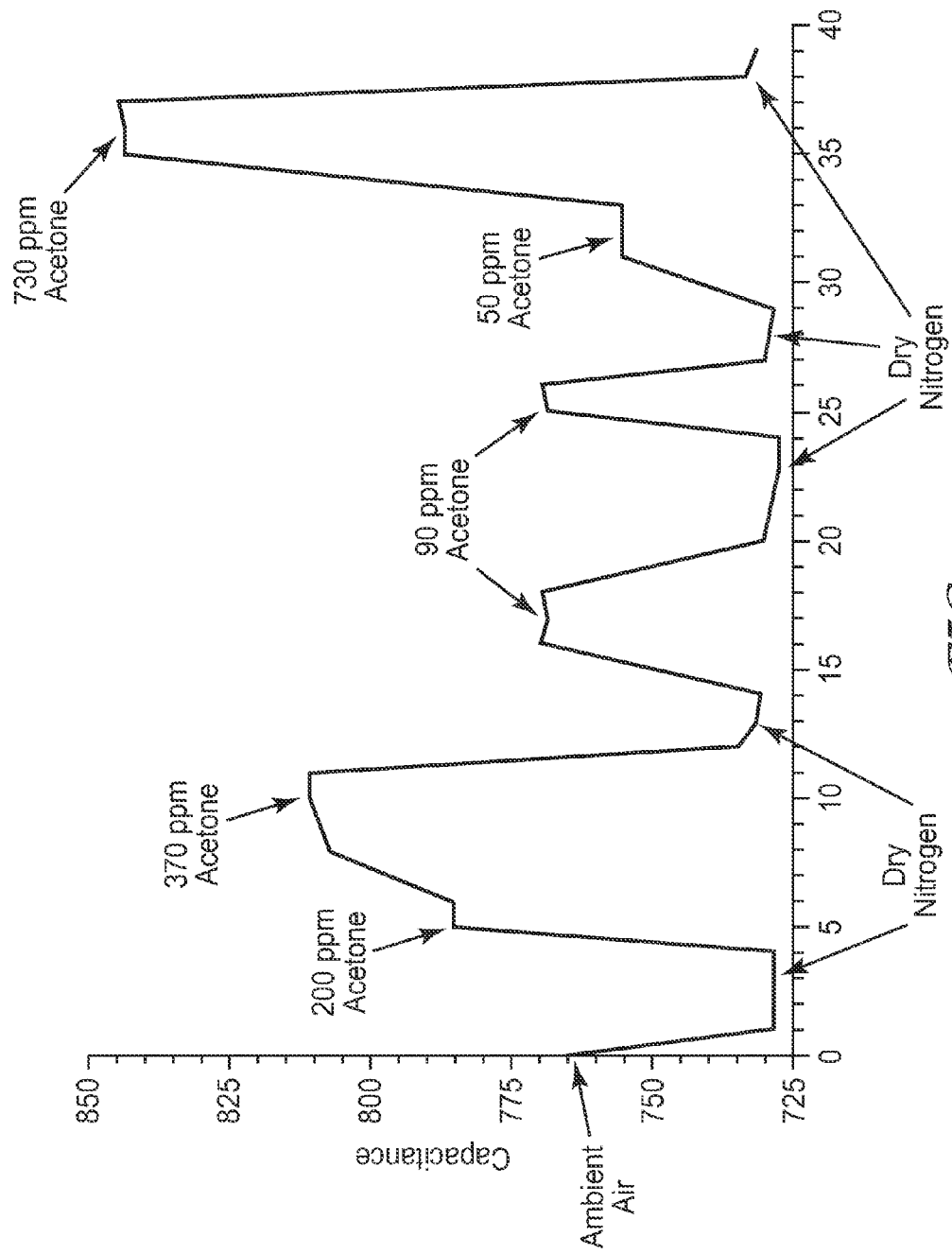
FIG. 4 is a plot of the measured capacitance of an exemplary sensing element of a parallel-plate configuration, as a function of time of exposure to various levels of an organic analyte.

A simple flow-through custom built delivery system was used to deliver known concentrations of acetone to the sample for measurement. Teflon tubing was used throughout the delivery system. Nitrogen was sparged through a container that contained acetone in liquid form and held at a constant temperature as to provide a nitrogen stream that was saturated with acetone. The liquid acetone was kept at a constant temperature using a chiller from Fisher Scientific, and the temperature at which to keep the chiller in order to create a saturated gaseous stream of acetone was calculated using the Handbook of Vapor Pressure (Yaws, C.I. Gulf Publishing: Houston, 1994). The saturated gaseous acetone stream was diluted with additional nitrogen by use of a series of mass flow controllers. The concentration of acetone in the gaseous stream was calibrated by use of an infrared spectrometer (available under the designation Miran Sapphire from ThermoElectron of Waltham, Mass.). The gaseous acetone stream was introduced into a sample chamber (held at controlled temperature) containing Sample 1. The first and second electrodes of the sample were connected to an operating circuit that comprised an LCR meter (available under the designation Instek Model 821 LCR meter from Instek America, Corp. Chino, Calif.) using alligator clips. The changes in capacitance (in picoFarads) of the sample were monitored at a frequency of 1 kilohertz at specific time intervals during the entire course of the vapor test (as shown in FIG. 4).

The sample was first placed in the unsealed test chamber in order to measure the initial capacitance of the sample at ambient conditions (room air). The sample was then exposed to dry nitrogen (approximately 8% relative humidity and 20° C.) starting at time=0. The test chamber was then sealed and a gaseous nitrogen stream containing approximately 200 ppm of acetone was introduced into the test chamber for a first period of time. After this, the sample was exposed to a gaseous dry nitrogen stream containing acetone at approximately 370 ppm for a period of time. Then, the test chamber was returned to a dry nitrogen environment. After this, the sample was successively exposed to approximately 90 ppm acetone, approximately 90 ppm acetone (again), then approximately 50 ppm acetone, with the sample exposed to an acetone-free gaseous dry nitrogen stream between these exposures. After the exposure to approximately 50 ppm acetone, the sample was exposed to approximately 730 ppm acetone, after which the sample was again exposed to an acetone-free stream of dry nitrogen.

A number of embodiments of the invention have been described. Nevertheless, it will be understood that various modifications may be made without departing from the invention. Accordingly, other embodiments are within the scope of the following claims.

What is claimed is:

1. A sensor for sensing an organic chemical analyte, comprising:
a sensing element that comprises a first electrode and a second electrode and a microporous, hydrophobic, analyte-responsive dielectric material disposed at least in proximity to the first and second electrodes, wherein the microporous, hydrophobic analyte-responsive dielectric material comprises an amorphous random covalent network comprising at least about 30% carbon, and having a mean pore size of less than about 10 nm and a porosity of at least about 20%, and that is a plasma-deposited network; and,
an operating circuit in electrical communication with the first and second electrodes, wherein the operating circuit is capable of applying a voltage to the first and second electrodes and is capable of detecting a change in an electrical property of the sensing element.

2. The sensor of claim 1 wherein the amorphous random covalent network also comprises silicon, oxygen, and hydrogen.

3. The sensor of claim 1 wherein the amorphous random covalent network comprises essentially 100% carbon.

4. The sensor of claim 1 wherein the amorphous random covalent network comprises a porosity of at least about 30%.

5. The sensor of claim 1 in which at least one of the electrodes is permeable to an organic chemical analyte.

6. The sensor of claim 5 wherein the permeable electrode comprises a discontinuous layer of conductive material.

7. The sensor of claim 1 wherein the sensing element comprises a parallel-plate capacitor configuration.

8. The sensor of claim 1 wherein the sensing element comprises an interdigitated capacitor configuration.

9. The sensor of claim 1 wherein the sensing element comprises a cover layer in proximity to at least one of the electrodes, the cover layer being permeable to an organic chemical analyte.

10. The sensor of claim 1 wherein the amorphous random covalent network comprises about 100% carbon.

11. A sensor for sensing an organic chemical analyte, comprising:
a sensing element that comprises a first electrode and a second electrode and a microporous, hydrophobic, analyte-responsive dielectric material disposed at least in proximity to the first and second electrodes, wherein the microporous, hydrophobic analyte-responsive dielectric material comprises an amorphous random covalent network that comprises essentially 100% carbon, and having a mean pore size of less than about 10 nm and a porosity of at least about 20%; and,
an operating circuit in electrical communication with the first and second electrodes, wherein the operating circuit is capable of applying a voltage to the first and second electrodes and is capable of detecting a change in an electrical property of the sensing element.

12. The sensor of claim 11 wherein the amorphous random covalent network comprises a porosity of at least about 30%.

13. The sensor of claim 11 in which at least one of the electrodes is permeable to an organic chemical analyte.

14. The sensor of claim 13 wherein the permeable electrode comprises a discontinuous layer of conductive material.

15. The sensor of claim 11 wherein the sensing element comprises a parallel-plate capacitor configuration.

16. The sensor of claim 11 wherein the sensing element comprises an interdigitated capacitor configuration.

17. The sensor of claim 11 wherein the sensing element comprises a cover layer in proximity to at least one of the electrodes, the cover layer being permeable to an organic chemical analyte.

* * * * *

UNITED STATES PATENT AND TRADEMARK OFFICE
CERTIFICATE OF CORRECTION

PATENT NO. : 8,378,694 B2  
APPLICATION NO. : 12/681758  
DATED : February 19, 2013  
INVENTOR(S) : Moses M David Page 1 of 1

It is certified that error appears in the above-identified patent and that said Letters Patent is hereby corrected as shown below:

Title Page, Column 1 item 65
Below Prior Publication, US2011/0031983 A1, Feb. 10, 2011, insert
-- Provisional Application No. 60/977,715, filed on Oct. 5, 2007 --.

Title Page, Column 2 item 56 (Other Publications)
Line 1, Delete "Poly[-(trimethylsilyl)-1-propyne]" and insert
-- Poly[1-(trimethylsilyl)-1-propyne] --, therefor.

Title Page, Column 2 item 56 (Other Publications)
Line 2, Delete "proprties" and insert -- properties --, therefor.

In the Specification

Column 1, Page 2
Below the Title, insert

-- CROSS-REFERENCE TO RELATED APPLICATION

This application is a national stage filing under 35 U.S.C. 371 of PCT/US2008/078281, filed September 30, 2008, which claims priority to U.S. Provisional Application No. 60/977,715 filed October 5, 2007, the disclosure of which is incorporated by reference in its/their entirety herein. --.

Signed and Sealed this  
Sixth Day of August, 2013

Teresa Stanek Rea  
*Acting Director of the United States Patent and Trademark Office*